(12) United States Patent
Los (10) Patent No.: US 8,093,271 B2
(45) Date of Patent: Jan. 10, 2012

(54) ANTI-ACID PHARMACEUTICAL COMPOSITION IN POWDER FORM AND PROCESS FOR MAKING IT

(75) Inventor: Mario Atilio Los, Buenos Aires (AR)

(73) Assignee: Laboratorios Bago S.A., Buenos Aires (AR)

( * ) Notice: Subject to any disclaimer, the term of this patent is extended or adjusted under 35 U.S.C. 154(b) by 246 days.

(21) Appl. No.: 12/643,095

(22) Filed: Dec. 21, 2009

(65) Prior Publication Data

US 2010/0160382 A1 Jun. 24, 2010

Related U.S. Application Data

(62) Division of application No. 11/810,453, filed on Jun. 5, 2007, now Pat. No. 7,968,118.

(30) Foreign Application Priority Data

Jun. 5, 2006 (AR) .......................... P20060102333

(51) Int. Cl.
 *A61K 31/4439* (2006.01)
 *A61P 1/04* (2006.01)

(52) U.S. Cl. ....................................... 514/338

(58) Field of Classification Search .................. None
 See application file for complete search history.

(56) References Cited

U.S. PATENT DOCUMENTS

| 4,744,986 A | 5/1988 | Luber et al. |
| 4,786,505 A | 11/1988 | Lovgren et al. |
| 6,183,776 B1 | 2/2001 | Depui et al. |

FOREIGN PATENT DOCUMENTS

| EP | 0813424 | 11/2002 |
| GB | 2189698 | 11/1987 |
| WO | 98/23272 | 6/1998 |
| WO | 2004/089340 | 10/2004 |
| WO | 2005/007117 | 1/2005 |
| WO | 2005/032554 | 4/2005 |

OTHER PUBLICATIONS

A.M. Sakr et al., Effect of the Technique of Incorporating Sodium Alignate on its Binding and/or Disintegrating Effectiveness in Sulfathiazole Tablets, Pharm Ind., 1978, pp. 1080-1086, 40 (10), Asyot, Egypt.
A. Pilbrant et al., Development of an oral formulation of omeprazole, Scandinavian Journal of Gastroenterology, 1985, pp. 113-120, 20 (Suppl. 108), Sweden.
European Search Report for European Patent Application No. 07 38 0159, dated Apr. 10, 2008.
K.G. Mandel et al., Review article: alginate-raft formulations in the treatment of heartburn and acid reflux, Aliment Pharmacol Ther 2000, Jan. 12, 2000, pp. 669-690, vol. 14, Blackwell Science Ltd., U.S.A.
Per Lindberg et al., The Mechanism of Action of the Gastric Acid Secretion Inhibitor Omeprazole, Journal of Medicinal Chemistry, 1986, pp. 1327-1329, vol. 29, No. 8, the American Chemical Society.
Sir Colin Dollery et al., Therapeutic Drugs—Omeprazole, 1991, pp. O17-O20, vol. 2, 1st edition, Churchill Livinstone, United Kingdom.
Robert A. Quercia et al., Stability of omeprazole in an extemporaneously prepared oral liquid, Am J Health-Syst Pharm, Aug. 15, 1997, pp. 1833-1836, vol. 54, American Society of Health-System Pharmacists, Inc.
Jeffrey O. Phillips et al., A prospective study of simplified omeprazole suspension for the prophylaxis of stress-related mucosal damage, Crit Care Med, 1996, pp. 1793-1800, vol. 24, No. 11, Williams & Wilkins.
Dr. Jose Rafael Blengio Pinto et al., Comparacion de las propiedades de los antagonistas de los receptores H2 de histamina, Goodman & Gilman, Las Bases Famacologicas De La Terapeutica, 2003, p. 1025, Volumen 1, Decima Edicion, McGraw Hill, Argentina.
Gaviscon Infant, mims—Monthly Index of Medical Specialists, Sep. 2001, p. 14, Eisai Ltd.
Man Tang et al., Bioadhesive oesophageal bandages: protection against acid and pepsin injury, international journal of pharmaceutics, 2005, pp. 169-177, vol. 292, Elsevier B.V., United Kingdom.
Gaviscon Advance, Summary of Product Characteristics last updated on the eMC: Sep. 19, 2005, Forum Health Products Limited, United Kingdom.
Yajaman Sudhakar et al., Buccal bioadhesive drug delivery—A promising option for orally less efficient drugs, Journal of Controlled Release, 2006, pp. 15-40, vol. 114, Issue 1, Elsevier B.V.—Abstract Only.

*Primary Examiner* — Robert A Wax
*Assistant Examiner* — Danah Al-Awadi
(74) *Attorney, Agent, or Firm* — Bachman & LaPointe, P.C.

(57) ABSTRACT

An anti-acid pharmaceutical composition for the rapid and prolonged neutralization of gastric acidity with mucosa-protecting activity in powder form to prepare, by dispersion in water, a pharmaceutical solution or suspension for oral use characterized in that the composition includes sodium alginate; an anti-acid soluble agent or a combination of anti-acids; an inhibitor of proton pump; diluent and sweetening agents, wherein a) at least 30% of sodium alginate present in the formulation along with the total of the inhibitor of proton pump are homogeneously distributed over the surface of the total soluble anti-acid agent of the combination of anti-acids of the composition; and b) the rest, about 70%, of sodium alginate present in the formulation contains a percentage of humidity of less than 2%.

23 Claims, 3 Drawing Sheets

ANTI-ACID PHARMACEUTICAL COMPOSITION IN POWDER FORM AND PROCESS FOR MAKING IT

CROSS REFERENCE TO RELATED APPLICATIONS

This application is a divisional application of U.S. application Ser. No. 11/810,453 filed Jun. 5, 2007.

FIELD OF THE INVENTION

The present invention refers to a pharmaceutical composition for oral use and a process for making it containing sodium alginate, a proton pump inhibitor and one or more soluble or partially soluble anti-acids for the treatment of hyperacidity with immediate or long lasting therapeutic activity.

BACKGROUND

Hyperacidity is an entity which is present in various digestive tract pathologic states. In each case it appears with proper intensity, duration and characteristics. It is present in the erosive esophagitis, pathologic hypersecretion such as Zollinger-Ellison syndrome, duodenal erosions or gastric ulcers associated with the administration of non-steroidal anti-inflammatory drugs, infection due to *Helicobacter pylori*, ulcer due to stress (Dollery, Colin et al.; *Therapeutic Drugs* Vol. 2; Edic. Churchill Livingstone, UK, 1991), which is incorporated by reference herein in its entirety), consumption of substances harmful to the digestive apparatus (for example, coffee, alcohol, and the like).

The hyperacidity caused by the abnormal or excessive production of acid results in inflammation of the stomach or gastritis. It also results in esophagic involvement when it produces reflux from the stomach to the esophagus.

Numerous drugs have shown to be effective for controlling or suppress hyperacidity as a symptom.

Such drugs have particular characteristics regarding behavior, efficiency and duration of action.

Thus, for example:

1. Anti-Acids:

Are generally inorganic soluble or little soluble salts, alone or in combination. Among them are: calcium and magnesium carbonate, sodium bicarbonate, aluminum hydroxide, aluminum phosphate, and the like.

After their entering into the stomach they neutralize immediately gastric acidity. They act in situ and do not require prior absorption.

They have an immediate therapeutic effect though they are short acting.

2. Alginic Acid and its Sodium and Magnesium Salts:

The alginic acid and its salts associates with sodium and potassium bicarbonate have shown that, after entering the stomach environment they form a viscous suspension (or a gel) exerting protecting activity over gastric mucosa. The scientific and patent literature on its activity is wide. Thus, for example:

Mandel K. G.; Daggy B. P.; Brodie D. A; Jacoby, H. L., 2000. Review article: Alginate-raft formulations in the treatment of heartburn and acid reflux. Aliment. Pharmacol. Ther. 14 669-690[.], which is incorporated by reference herein in its entirety;

Bioadhesive oesophageal bandages: protection against acid and pepsin injury. Man Tang, Peter Dettmar, Hannah Batchelor—International Journal of Pharmaceutics 292 (2005)-169-177, which is incorporated by reference herein in its entirety.

The number of commercially available alginate products for therapeutic use worldwide is also important. Thus, for example, in MIMS (Monthly Index of Medical Specialities) of Great Britain there are mentioned some pharmaceutical products containing sodium alginate and potassium bicarbonate (Gaviscon Advance) for heat, esophagic reflux and dyspepsia, Liquid Gaviscon containing sodium alginate, sodium bicarbonate and calcium carbonate. There is also a composition formed by sodium and magnesium alginate (Gaviscon Infant).

3. Antagonists of H2 Histamine Receptors:

They reduce the production of histamine which stimulates the formation of acid in the stomach due to the selective blockade of H2 receptors.

Compared with prior art anti-acids, they have longer effect and duration of action (6 to 12 hours) (Goodman y Gilman. *Las bases farmacolóogicas de la terapéutica*; Vol I, pág. 1025, X Edición, Mc. Graw Hill, 2003), which is incorporated herein by reference in its entirety.

Preferred examples are: cimetidine, nizatidine, famotidine and ranitidine.

4. Inhibitors of Proton Pump:

This is the most modern pharmacologic group for this kind of therapeutics. They act by selectively and specifically blocking the $H^+$—$K^{+-}$-ATPase enzyme of stomach parietal cell. They cause a marked reduction of the production of acid by the stomach parietal cells.

Thus, for example, in patients with duodenal ulcer, oral administration of 20 mg of omeprazole keeps the gastric pH in 3 or greater than 3 for 17 hours. The maximum effect is reached within 4 days of treatment.

Preferred examples are: omeprazole, lansoprazole, esomeprazole, pantoprazole, rabeprazole and the like.

The use of each one of the above mentioned alternatives is associated with the specific characteristic and intensity of the disease state causing hyperacidity.

Anti-acids and alginates have shown immediate effect as they act in the stomach and do not require prior absorption. The control of hyperacidity is rapid but with short duration.

On the other hand, the inhibitors of proton pump do not have immediate effect. Their effect is long because they necessarily have to be absorbed in order to exert their activity. Thus, for example, the absorption of omeprazole is done in the small intestine and is completed by 3-6 hours. Such a behavior causes some technical inconveniencies for the design of a pharmaceutical composition. Since:

a) Omeprazole requires, in fasting state, at least 20 to 30 minutes to reach the intestine.

b) It also requires an additional time for its intestinal absorption.

c) Since it is a scarcely stable substance in acid medium, while it is in the gastric environment, it is easily destructed before it reaches the intestine and, therefore, it should necessarily be protected from said gastric acidity.

The low stability of omeprazole in an acid medium has been widely documented from 1985 (Pilbrant and Cederberg—*SCAND. J GASTROENTEROLOGY* (1985), 20 (Suppl. 108)—p. 113-120) (Lindberg Per et al.—*J MED. CHEM* (1986), 29—p. 1327-1329), which is incorporated by reference herein in its entirety. Its half life in water and at a pH of 4 is lower than 10 minutes, being it of about 14 hours at a pH near 7.

Numerous alternatives have been explored to elaborate stable pharmaceutical forms mainly to solve the 2 most important problems (pH and moisture) affecting the stability of omeprazole. Thus, for example:

Britain patent GB No 2,189,698 (1987) describes the elaboration of an oral form of omeprazole characterized for having a core formed by the active principle (omeprazole) with a basic reactant and said core is coated by one or more protecting layers, which are water soluble, and an outer layer of enteric coating, which is incorporated herein by reference in its entirety. The proceeding and the obtained products showed an appropriate resistance to gastric fluid and a good stability of the active principle they contain (omeprazole) within gastric fluid and also when they are stored for a long period of time.

Phillips J. et al. have described a method for preparing omeprazole suspensions using sodium bicarbonate and flavored for children (Phillips J et al.—*A prospective study of simplified omeprazole suspension for the prophylaxis of stress-related mucosal damage. Crit. Care Med* 1996; 24:1793-800), which is incorporated herein by reference in its entirety).

Before, in 1997 Quercia R. et al., demonstrated that it is possible to extemporaneously prepare a suspension with 2 mg/ml of omeprazole for oral use and which is stable for 14 days at 24° C. from capsules containing omeprazole granules with enteric coating and a solution of sodium bicarbonate (Quercia R. et. al.—Stability of omeprazole in an extemporaneously prepared oral liquid—Vol. 54, Aug. 15, 1997, Am. J. Health—Syst. Pharm.—p. 1833, which is incorporated by reference herein in its entirety).

WO 2005/007117 A2 (2005) describes a powder formulation for suspension containing at least a soluble anti-acid, an inhibitor of the proton pump and a suspension agent preferably xanthan gum, which is incorporated by reference herein in its entirety. This patent remarks the importance of the particle size of the proton pump inhibitor and the presence of the suspension agent in the formulation in order to obtain a good suspendability. It is also noted that the presence of anti-acids in the composition increases the pH level of the gastrointestinal fluid, thus inhibiting the degradation of the proton pump inhibitor in the gastric environment.

EP 0813424 B1 (2002) describes a multi-particulate tablet composition containing an inhibitor of proton pump along with alginate and one or more anti-acid agents, which is incorporated by reference herein in its entirety. The inhibitor of proton pump is under the form of pellets with enteric coating. This fact makes necessary the addition of a prior and specific industrial stage for the elaboration of said pellets.

The above mentioned proceedings and most of those described by the literature mention various conditions needed to assure the stability and efficiency of the inhibitor of proton pump. For example, prior elaboration of enteric pellets, micronization of the inhibitor, addition of suspendibility agents, addition of basic substances to the pellets, etc. All of them require industrial operations and additional equipment (micronizers, fluid bed, dryers, etc.) and generally a much more extended time than the one necessary with the current proceedings for the elaboration of the above described pharmaceutical forms.

The association of the present invention (sodium alginate, soluble anti-acid and inhibitor of proton pump) only uses the routine industrial equipment for the elaboration of pharmaceutical forms destined for oral administration.

BRIEF DESCRIPTION OF THE INVENTION

The present invention refers to a new association for oral use and a proceeding for elaborating it containing sodium alginate, an inhibitor of proton pump and one or more soluble or partially soluble anti-acids for the treatment of hyperacidity and with immediate or long lasting activity.

The anti-acid and the sodium alginate of the composition rapidly neutralize hyperacidity acting directly in the digestive tract with no need of prior absorption. The inhibitor of proton pump, prior absorption at intestinal level, confers the pharmaceutical composition a prolonged control of hyperacidity.

The proceeding for the elaboration of the association, object of the present invention, is mainly featured by 3 element of practical importance. Among them are:

1. Make a wet granulation of the inhibitor of proton pump with the totality of the anti-acid agent or agents of the composition, other ingredients and up to 30% of the composition alginate, then proceeding to dry.

It is an objective of this operation to contribute with the best stability of the inhibitor of proton pump through the homogeneous distribution of said inhibitor and part of the alginate of the composition (or internal alginate) over the surface of the anti-acid agent.

2. Afterwards mixing the above mentioned mixture with the rest of sodium alginate present in the formulation and other ingredients thereof.

In order to favor the rapid dispersion of the remaining sodium alginate of the composition (or external alginate) and rapidly increase the viscosity of the solution or suspension when mixing the composition with water prior to the intake.

3. Using, as external sodium alginate, specifically a sodium alginate characterized by its low molecular weight, granular structure and prior drying to an humidity of less than 2% in order to favor the rapid formation of an homogeneous suspension of all the ingredients of the composition after its reconstitution with water or other drink. Preferably, less than 2 minutes.

The election of the ingredients of the formulation and the elaboration process have shown that they allow to obtain compositions for oral use with appropriate pharmaceutical and stability characteristics.

The details of one or more embodiments of the invention are set forth in the accompanying drawings and the description below. Other features, objects, and advantages of the invention will be apparent from the description and drawings, and from the claims.

DESCRIPTION OF DRAWINGS

Other advantages and characteristics of the invention will become evident from the following description in which, entirely from non-limitatively, are described some preferential embodiments of the invention, with reference to the appended drawings. The figures show.

DETAILED DESCRIPTION OF THE INVENTION

The industrial elaboration of a pharmaceutical composition in powder form destined to prepare, through dilution in water, a solution or suspension capable to rapidly neutralize gastric hyperacidity, having long-lasting anti-acid activity and certain protective capacity of gastric mucosa requires the presence of various ingredients with specific functions and determined thereon.

The present invention demands the presence in the pharmaceutical composition of:

1. An anti-acid which is soluble or partially-soluble in water:

The preferred ones are: Sodium or potassium bicarbonate, mixtures of sodium bicarbonate and carbonate, sodium bicarbonate associated with calcium and magnesium carbonate, sodium bicarbonate and calcium or aluminum hydroxide. These soluble or partially soluble anti-acids or combination thereof may be added in an amount of about 100 to 2000 mg per dosage unit.

2. Alginic acid or its sodium or magnesium salts.

3. An inhibitor of proton pump:

The preferred among them are: omeprazole, esomeprazole, lansoprazole, pantoprazole and rabeprazole. The proton pump inhibitor may be added in an amount of about 10 to about 80 mg per dosage unit.

4. Besides of excipients, sugar, binder, scents, sweetener and the like.

The scents which are used during the present invention may be in powder form or coated (For example: Trademark Durarome by the company FIRMENICH or the like).

It has been shown through experiments that the mere mixture of the ingredients of the composition is not enough for the elaboration of a suitable and stable pharmaceutical product.

The mere operation of mixing the ingredients leads to incorrect compositions. Generally, they are characterized by:

1. Formation of precipitates due to irregular gelification of alginic acid or salts thereof.

2. Low fluidity of the powder through the product dosing and packaging stages.

3. Lack of uniformity of the contents of each dosing unit.

4. Irregular distribution of the inhibitor of proton pump over the anti-acid of the composition.

5. Irregular stability of the inhibitor of proton pump in acid environment upon the reconstitution of the pharmaceutical composition with water an prior to its administration.

6. In general, the pharmaceutical forms obtained upon reconstitution with water or other drinks are not homogeneous. Therefore, they are not convenient for therapeutic use.

Surprisingly, it has been found and shown through experiments that it is possible to elaborate, appropriately, with the same ingredients, powdered pharmaceutical forms to be reconstituted through the proceeding object of the present invention.

The proceeding is original and requires various stages. They are:

A) Wet granulation:

It involves

1) Mixing 100% of the inhibitor of proton pump in a Collette granulator or similar, along with up to 30% of sodium alginate of the composition, 100% of the bicarbonate of the composition, 100% of the mannitol of the composition at maximum speed over 3 cycles of 4 minutes each one at room temperature.

2) Wet the resulting mixture in the same granulator (e.g.: Collette) at minimum speed, adding water with a peristaltic pump over 1 minute, then knead for 2 minutes at maximum speed. Using a total percentage in weight of water of no more than 10% of the total weight of the pharmaceutical composition.

B) Dry the Above Mixture in Fluid Bed, Under Vacuum or Under Normal Pressure:

At a temperature lower than 50° C. and until a residual humidity of 2% is obtained. Preferably lower than 0.7%.

C) Ground and Homogenize the Above Dry Granulate:

Using a Quadro Comill equipment with 991 micron conical sieve. Speed 2400 rpm and in dry room.

D) At the Same Time, Mix the Remaining Ingredients of the Preparation:

In Double Cone mixer (Size 2) at 60 rpm during 30 minutes in a dry room. Final humidity, due to loss upon drying, should not be higher than 1.5%.

E) Finally:

a) After performing the wet granulation (A), drying (B), grinding and homogenization (C), and mixing with the remaining ingredients (D).

b) Dose and package in an appropriate material.

c) Perform the following assessments: content of active principles, uniformity of the contents of the pharmaceutical composition and residual humidity.

Figure 1:
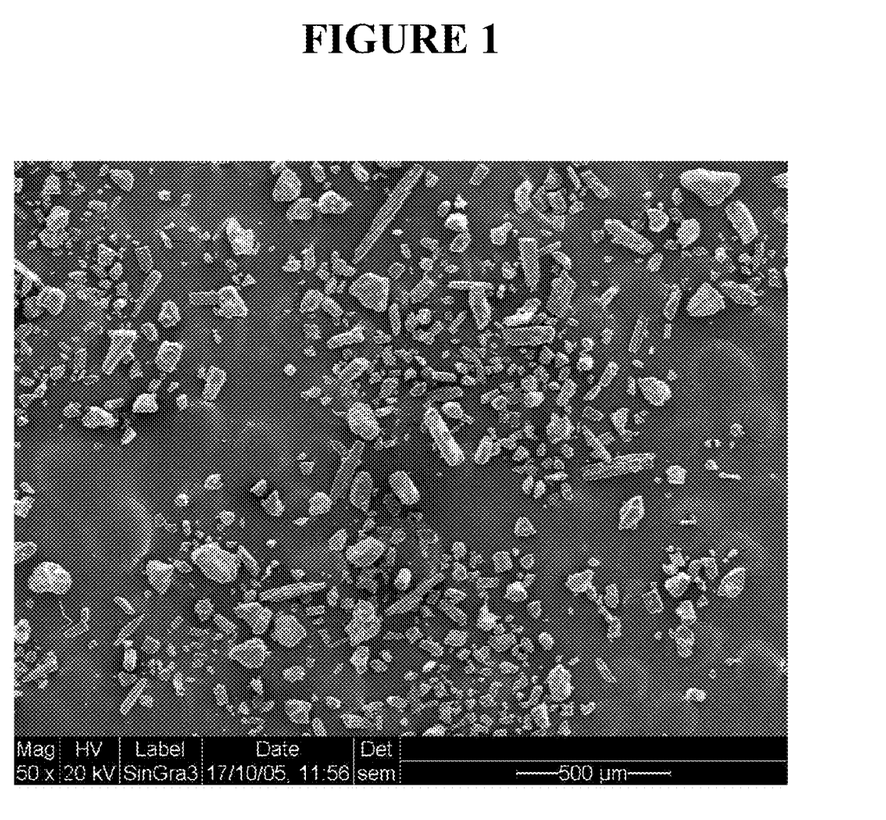
FIG. 1 is a microphotograph of a non-granulate mixture of sodium bicarbonate sodium alginate and omeprazole.
Figure 2:
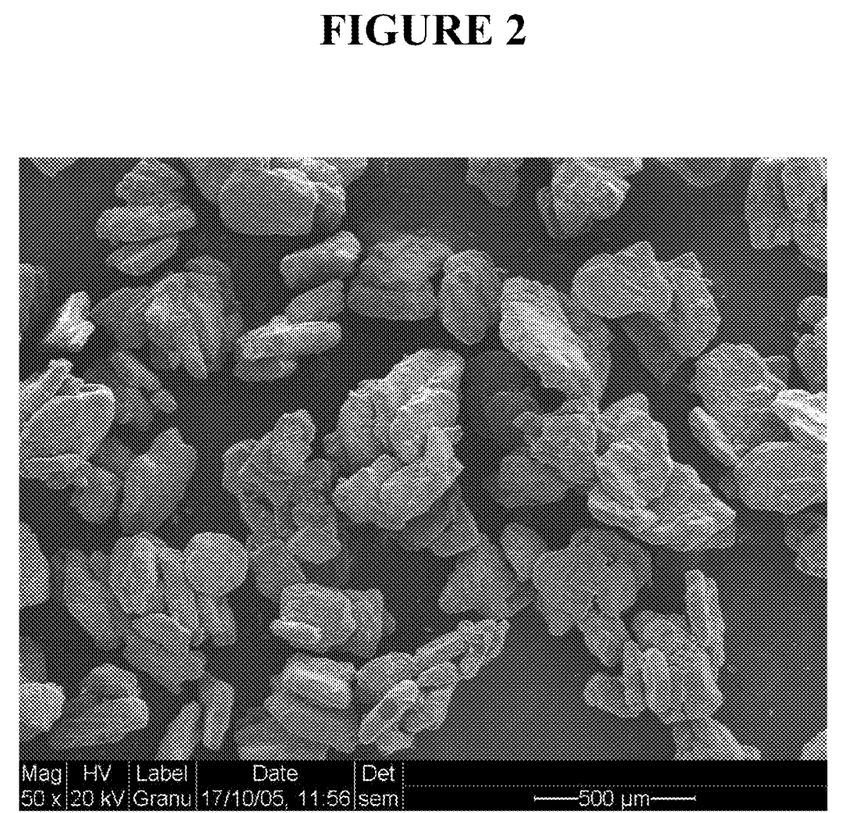
FIG. 2 is a microphotograph of a granulate mixture of water and sodium bicarbonate sodium alginate and omeprazole.

The enclosed photographs of electronic microscope allow for the observation of the difference in homogenization and distribution between:

A physical mixture of the ingredients (Sodium alginate, Omeprazole and Sodium bicarbonate) (FIG. 1) and, The obtained granulate (and with the same ingredients) through the above describe proceeding (FIG. 2).

The dosing and packaging of the composition, object of the present invention, may be performed, equally in:

A) Single dose Units, or either in

B) Multiple dose Units

In packages of 50-100 or 200 grams with airtight closure and attached powder metered-dose device. Corresponding to 10, 20 or 40 dosing units. One remarked and surprising aspect, due to its practical results, has been the election of sodium alginate to be used for the present invention.

The alginic acid and its sodium salt are linear copolymers of $\beta(1\rightarrow4)$-D-mannuronic acid and $\alpha$-L-guluronic acid. They may have variable morphologies and molecular weights. The molecular weight may range between 20,000 and 200,000. Such characteristics confer each of them particular properties.

Without being bond to theory, the sodium alginate used in the proceeding of this invention is characterized by having a low percentage of humidity of up to 2%, and preferably up to 0.7%, per drying before the incorporation of the preparation. The sodium alginate may be added in an amount of about 100 to about 500 mg per dosage unit.

Most of commercial basic alginates and alginic acid have high humidity (8 to 15%) and their use is not convenient directly in the formulation object of the present invention.

Besides, the content of sodium alginate of the pharmaceutical composition should be lower than 20% of the total weight of the formulation. Preferably, between 2 and 10% of the total weight thereof.

The sodium alginate added to the composition, besides of its therapeutic activity, supplies the composition with the following technical characteristics:

1) During the granulation the presence of up to 30% of total sodium alginate of the composition acts as a binder and notably improves the fluency of the mixture during the fractioning and packaging stages of the pharmaceutical product.

The binding property of alginates is well known and widely described in technical literature. E.g.:

(Sakr A M, Elsabbagh H M, Shalaby A H, *Effect of the technique of incorporating sodium alginate on its binding and/or disintegrating effectiveness in sulfathiazole tablets—PHARM IND.* (1978); 40 (10); 1080-1086), which is incorporated by reference herein in its entirety.

2) Also during wet granulation it favors the homogeneous distribution of the inhibitor of proton pump over the sodium bicarbonate and mannitol.

For the granulation state it is not necessary (although it is convenient, due to its alginate.

3) The second fraction of sodium alginate of the total in the composition should preferably be of low humidity, which assures 3 remarked characteristics:

a) Fast dissolution without the formation of clots or precipitates during the reconstitution of the powder in water. The practical use for the pharmaceutical form for oral administration.

b) Rapid increase of viscosity of the solution or suspension reconstituted with water. Favoring the homogeneous dispersion of the inhibitor of proton pump which is bond to the granulate crystals.

c) The rapid dispersion of sodium alginate (called "external") and which has been incorporated after the wet granulation also favors the anti-acid and muco-protective activity of this substance over gastric mucosa.

Another surprising and experimentally demonstrated aspect has been that wet granulation did not destroy the inhibitor of proton pump present in the granulate. Even in the presence of water and at a temperature of up to 50° at normal pressure during a relatively considerable drying time. Possible due to the formation of a protecting basic micro-environment generated by the sodium bicarbonate and the sodium alginate in intimate contact with such inhibitor of proton pump. This protection has been demonstrated and is mentioned in the Examples section.

It has also been indirectly demonstrated that the composition, due to its nature, protects the inhibitor of proton pump from gastric pH after the intake of the product for the time needed and enough to reach the first portion of the intestine, where the pH of the environment is compatible with the chemical stability of said inhibitor.

Thus, for example:

It has been observed through experiments, and it is so described in the Examples section, that the composition object of the present invention suitably supports the incorporation of up to 20 mEq of hydrochloric acid during 30 minutes (simulated gastric environment).

It has also been shown and it is so described in the Examples section that the powder stability and is suitable for human use under the form of extemporaneous suspensions.

It has been observed that the composition object of the present invention shows the following general characteristics and advantages:

1) When it is incorporated to a dosing unit at a volume of water of 30 to 100 ml under stirring it forms a rapid and homogeneous suspension.

2) The low molecular weight sodium alginate, preferably granular and previously dried to a humidity of less than 2% is rapidly and practically dispersed. It does not decant and contributes to an homogeneous suspension of the inhibitor of proton pump and other ingredients.

3) When the composition is added to a simulated gastric environment:

a) A pH of more than 6 is reached in less than 2 minutes.

b) When 0.1N hydrochloric acid is incorporated afterwards at 0.66 mEq/minute up to 20 mEquivalents, the pH is kept near 6 for about 30 minutes. This is the time needed and enough for the inhibitor of proton pump to reach the first portion of the small intestine, as observed in the Examples section below.

Figure 3:
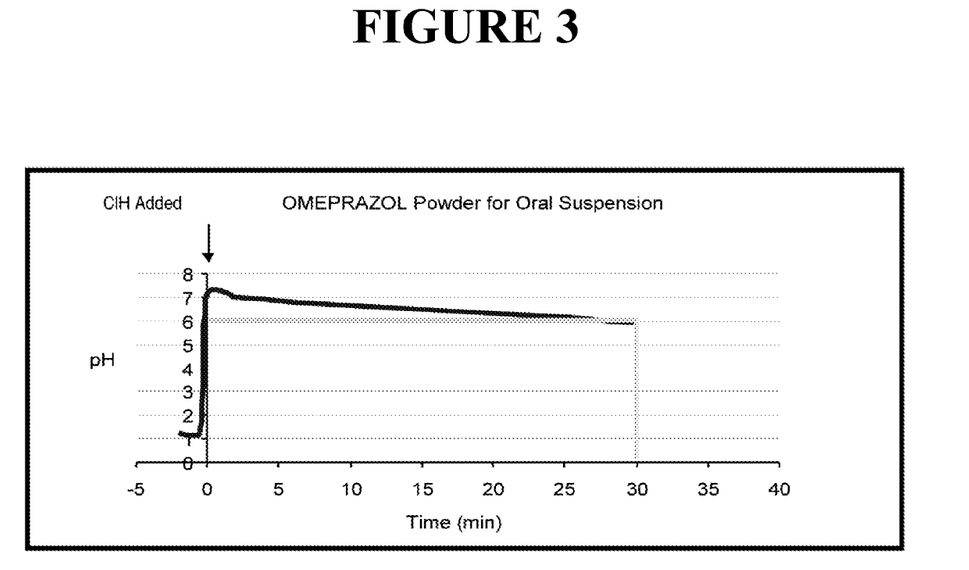
FIG. 3 is a graph representing the behavior of the single dose granulate containing 20 mg of omeprazole.

FIG. 3.

4) The stability of the inhibitor of proton pump is suitable, being, after 30 minutes higher than 95% and also 99%.

5) The addition of sodium alginate with the above mentioned characteristics gives certain flexibility to the formula:

a) It allows to modify the content of inhibitor of proton pump and other ingredients of the composition without altering neither its physical-chemical characteristics nor its stability.

b) And it meets, as mentioned above, 2 functions in the composition:

The addition of the rest of sodium alginate added during the wet granulation acts as a binder and improves flowability and uniformity of the contents of the composition, and possibly, along with the sodium bicarbonate present in the wet granulation it protects the inhibitor of proton pump.

The addition of the rest of sodium alginate up to 70% added afterwards acts as gelification agent, anti-acid and protector of the gastric mucosa.

6) The thus obtained pharmaceutical forms, reconstituted with water or other drinks, are homogeneous and are, therefore, convenient for their therapeutic use in human medicine.

7) With the same composition it is possible to elaborate pharmaceutical presentations: Single dose and Multiple dose.

8) The flexibility of the proceeding allows to elaborate Single and Multiple dose compositions with a different content of inhibitor of proton pump as required, for therapeutic reasons or due to the age of patients to whom the product is destined.

The following examples, without being limitating, show in practice the compositions and the practical forms of elaboration.

EXAMPLE 1

Granulate in Single Dose Bags for Oral Suspension Using Encapsulated Scents (E1) Formula Each Bag Contains:

| | |
|---|---|
| OMEPRAZOLE | 20 mg |
| SODIUM ALGINATE | 50 mg |
| MANNITOL | 50 mg |
| SODIUM BICARBONATE | 1680 mg |
| ANHYDROUS CORN STARCH | 160 mg |
| DRIED SODIUM ALGINATE | 200 mg |
| ENCAPSULATED STRAWBERRY SCENT | 75 mg |
| ENCAPSULATED BANANA SCENT | 75 mg |
| SUCRALOSE | 40 mg |
| SUGAR GRADE q.s. | 5000 mg |

Stages:

Stage I: Wet Granulation:

The granulate was prepared in an amount enough for 600 bags with:

| | |
|---|---|
| OMEPRAZOLE | 12 g |
| SODIUM BICARBONATE | 1008 g |
| MANNITOL | 30 g |
| SODIUM ALGINATE | 30 g |
| DISTILLED WATER (granulating liquid) | 160 mg |

Substances to be granulated were placed in a Collette granulator (omeprazole, sodium bicarbonate, mannitol and sodium alginate).

3 mixing runs were performed of 4 minutes each at maximum speed.

Distilled water was added through a peristaltic pump for 1 minute, granulating at minimum speed, and finally one run of mixing was applied at maximum speed.

Stage II: Drying, Milling and Homogenization of the Granulate

The obtained wet granulate was dried in a fluid bed at 50° C. for 3 hours until the residual humidity determined by loss upon drying was between 0.5 and 1.5%.

The dry granulate was milled and homogenized in Quadro Comill Mill (sieve: 991 microns, speed: 2400 rpm).

The thus obtained granulate showed the following approximate particle size distribution. Retained mesh 30 (600 microns) less than 1% Retained mesh 140 (100 microns) more than 95%

Stage III: Mixing with the Other Ingredients of the Composition

Dried Sodium alginate: 100 grams of sodium alginate were first dried at 70° C. under vacuum until a residual humidity of less than 2% was obtained.

The dried omeprazole granulate obtained in stage II above (weight 1080 g) was mixed with the following ingredients of the formulation:

| | |
|---|---|
| DESICCATED SODIUM ALGINATE | 120 g |
| CORN STARCH | 96 g |
| ENCAPSULATED STRAWBERRY SCENT | 15 g |
| ENCAPSULATED BANANA SCENT | 15 g |
| SUCRALOSE | 24 g |
| SUGAR | 1650 g | in Double Cone mixer for 30 minutes at 60 rpm.

The dosage (in single dose bags) and final packaging was performed in Rovena equipment using the appropriate foil: triple foil (paper-aluminum-polyethylene)

Content weight per bag: 5 g dose, which contains about 5% to about 10% of sodium alginate, about 33.6% of sodium bicarbonate and about 0.4 to about 0.8% of a proton pump inhibitor.

Humidity: 0.5 to 1.5%

Aqueous activity: 0.4 to 0.6% Rotronic hydroscop BT.

Approximate Particle Size Distribution:

Retained mesh 30 (600 microns) less than 1%

Retained mesh 140 (100 microns) more than 95%

The dispersion of the content of a bag (5 g) in about 30 ml of water was rapid, homogeneous and demanded less than 2 minutes.

[-] The taste of the dispersion was good.

EXAMPLE 2

Granulate in Single Dose Bags Using Non-Encapsulated Scents (for Example: Strawberry-Banana) (E2)

The proceeding and ingredients stated in Example 1 were used, except that the scents were not encapsulated. 600 bags were prepared.

Tests:

A) Corresponding to Intermediates Prepared According to Examples 1 and 2, and from Stage I (Wet Granulation) and Stage II (Drying, Milling And Homogenization)

A1: Assay: Content of Omeprazole in Granulates Obtained According to Example I and Example II Conditions:

Mobile phase: Acetonitrile: phosphate buffer pH 7.2 (35.65)

Temperature: 25° C.

Flow rate: 1 ml/min.

Pressure: 1400 PSI

Reading wave length: 300 nm

| | Mean Area | Response Factor |
|---|---|---|
| Reference 1* | 8918.7 | 0.000175 |
| Reference 2 | 9791.4 | |

*Omeprazole

| | Mean Area | % omeprazole | Weight (g) |
|---|---|---|---|
| E 1 | 9149.92 | 100.72 | 1.81 |
| E 2 | 8976.12 | 99.42 | 1.8 |

E 1: Granulate of omeprazole ex. 1
E 2: Granulate of omeprazole ex. 2

Samples were placed in a 25 ml volumetric flask and were brought to volume with diluent*.

* Diluent: 0.01M Sodium borate—Acetonitrile (3:1).

It was sonicated in a Test-Lab for 15 minutes, allowed to cool and then it was magnetically stirred for 15 minutes.

One portion was filtered through nylon filter (0.45 μm) and a 2 in 10 dilution was preformed with diluent*.

A2: Stability of the Granulates with Omeprazole Obtained in Examples 1 and 2.

Samples of both granulates were placed in caramel-colored bottles on the stove at 60° for 15 days.

The content of omeprazole was determined by HPLC:

Conditions:

Mobile phase: Acetonitrile: phosphate buffer pH 7.2 (35.65)

Temperature: 25° C.

Flow rate: 1 ml/min.

Pressure: 1400 PSI

Reading Wave length 300 nm

| Sample | % Omeprazole (Time zero) | % Omeprazole (15 days) |
|---|---|---|
| Ex. 1 Granulate | 99.6 | 100.1 |
| Ex. 2 Granulate | 98.3 | 94.8 |

It was seen that under the wet granulation conditions, subsequent drying at 50° C. and storage at 60° C./15 days, the stability of omeprazole and physical appearance of the composition were satisfactory.

B) Corresponding to End Product (Granulate in Single Dose Bags for Oral Suspension) Elaborated According to Stages 1, II and III Described in Examples 1 and 2).

B1: Assay of the Granulates in Single Dose Bags for Oral Suspension

Conditions:
Mobile Phase: Acetonitrile: phosphate buffer
pH 7.2 (35.65)
Temperature: 25° C.
Flow rate: 1 ml/min.
Pressure: 1400 PSI
Reading wave length: 300 nm

|  | Mean Area | Response Factor |
|---|---|---|
| Reference 1* | 5743.2 | 0.000418 |
| Reference 2 | 5351.7 |  |

*Omeprazole

|  | Mean Area | % omeprazole | Weight (g) |
|---|---|---|---|
| Example 1 | 4914.8171 | 102.14 | 5.11 |
| Example 2 | 5109.0681 | 101.22 | 5.36 |

Ex. 1: Single dose Bag with Encapsulated Scents (Strawberry-Banana)
Ex. 2: Single dose Bag with Non-Encapsulated Scents (Strawberry-Banana)

Samples were placed in a 100 ml volumetric flask and 50 ml of diluent were added*.
* Diluent: 0.01M Sodium borate—Acetonitrile (3:1).

It is sonicated for 15 minutes, cooled and brought to volume with Diluent. It is magnetically stirred for 15 minutes and then filtered through nylon 0.45 μm.

B 2: Uniformity of the Content of Omeprazole in Granulates in Single Dose Bags for Oral Suspension:

The content of omeprazole is determined according to the above stated conditions.

Results were as follows:

| Sample | Mean Area | Weight | % omep. |
|---|---|---|---|
| M1 | 4786.85 | 4.9886 | 99.1 |
| M2 | 4793.07 | 4.9442 | 100.1 |
| M3 | 4846.00 | 5.0436 | 99.2 |
| M4 | 4970.81 | 5.1499 | 99.7 |
| M5 | 4700.41 | 4.8969 | 99.5 |
| M6 | 4686.01 | 4.8263 | 100.2 |
| M7 | 4736.74 | 5.0025 | 97.8 |
| M8 | 4588.87 | 5.2330 | 90.5 |
| M9 | 4627.41 | 4.8709 | 98.1 |
| M10 | 4700.63 | 4.9078 | 98.9 |

AVERAGE: 98.34%
Variation coefficient: 2.89
M1 to M10: Correspond to bags with single dose granulate containing powdered non-coated scents.

It is observed that the pharmaceutical composition obtained through the above described elaboration proceeding has a very good uniformity of omeprazole contents.

B 3: Behavior of the Single Dose Granulate in Bags for Oral Suspension Containing to 20 mg of Omeprazole in Simulated Gastric Environment a) The total content of one bag (5 g) dispersed in water was added to 250 ml of 0.01 N HCl. Every 2 minutes (for a total of 30 minutes), addition of 0.1N hydrochloric acid was continued until the equivalent of 20 mEq of HCl was completed, measuring the pH continuously.

It is observed that at 30 minutes the pH is near 6 and it allows to keep the stability of the inhibitor of proton pump (omeprazole).

In FIG. 3: The change in pH is observed for the simulated gastric environment after the addition of the composition and throughout the 30 minutes of addition of 0.1 N hydrochloric acid.

b) After 30 minutes samples were extracted from the assayed solution and the content of omeprazole is determined (Method: HPLC according to Example II-C). The content was stable (99% of the starting amount of omeprazole present in the bag).

EXAMPLE 3

Single Dose Granulate in Bags for Oral Suspension Containing, Respectively, 30 and 40 mg of Omeprazole

|  | (A) | (B) |
|---|---|---|
| OMEPRAZOLE | 30 mg | 40 mg |
| SODIUM BICARBONATE | 1680 mg | 1680 mg |
| SODIUM ALGINATE | 50 mg | 50 mg |
| DESICCATED SODIUM ALGINATE | 200 mg | 200 mg |
| ANHYDROUS CORN STARCH | 160 mg | 160 mg |
| MANNITOL | 50 mg | 50 mg |
| SUCRALOSE | 40 mg | 40 mg |
| BITTER CORRECTOR | 4 mg | 4 mg |
| SUGAR q.s. | 5000 mg | 5000 mg |
| LIME-LEMON SCENT | 150 mg | 150 mg |
| ORANGE-LEMON SCENT | **** | 150 mg |

600 bags were prepared of each strength (30 and 40 mg de omeprazole) and controlled according to Example 1 and 2 (stages I, II and III).

EXAMPLE 4

Granulates in single dose bags were prepared for oral suspension according to the product stated in Examples I and II, containing the following inhibitors of proton pump: Lantoprazole, Esomeprazole and Pantoprazole.

The single dose bag compositions for each inhibitor of the proton pump are summarized in the following table:

| Composition | 1 | 2 | 3 | 4 | 5 | 6 | 7 | 8 | 9 |
|---|---|---|---|---|---|---|---|---|---|
| PANTOPRAZOLE | 20 | **** | **** | 20 | **** | **** | 40 | **** | **** |
| LANSOPRAZOLE | **** | 20 | **** | **** | 30 | **** | **** | 15 | **** |
| ESOMEPRAZOLE | **** | **** | 20 | **** | **** | 20 | **** | **** | 40 |
| SODIUM BICARBONATE | 1680 | 1680 | 1680 | 1680 | 1680 | 1680 | 1680 | 1680 | 1680 |

-continued

| Composition | 1 | 2 | 3 | 4 | 5 | 6 | 7 | 8 | 9 |
|---|---|---|---|---|---|---|---|---|---|
| SODIUM ALGINATE | 50 | 50 | 50 | 50 | 50 | 50 | 50 | 50 | 50 |
| DESICCATED SODIUM ALGINATE | 200 | 200 | 200 | 200 | 200 | 200 | 200 | 200 | 200 |
| DRY CORN STARCH | 160 | 160 | 160 | 160 | 160 | 160 | 160 | 160 | 160 |
| MANNITOL | 50 | 50 | 50 | 50 | 50 | 50 | 50 | 50 | 50 |
| SUCRALOSE | 40 | 40 | 40 | 40 | 40 | 40 | 40 | 40 | 40 |
| SUGAR q.s. | 5000 | 5000 | 5000 | 5000 | 5000 | 5000 | 5000 | 5000 | 5000 |
| LIME-LEMON | 150 | 150 | 150 | **** | **** | **** | **** | **** | **** |
| ORANGE-LEMON | **** | **** | **** | 75 + 75 | 75 + 75 | 75 + 75 | **** | **** | **** |
| BANANA-STRAWBERRY | **** | **** | **** | **** | **** | **** | 75 + 75 | 75 + 75 | 75 + 75 |

The suspension in water showed, in all the cases, good and fresh taste.

EXAMPLE 5

Granulate Multiple Dose Pharmaceutical Compositions for Oral Suspension which Active Principle is Either: Omeprazole, Esomeprazole, Lansoprazole or Pantoprazole They were prepared according to the proceedings stated in Examples I, II and IV for multiple dose compositions.

Said compositions or granulates elaborated according to the above were packaged in units (glass, high density polyethylene) and with air-tight closure. Preferably, with threaded closure.

In every case, the addition was of:

a) One bag with desiccating material (Silicagel) to preserve the contents of the humidity added during the packaging b) One unit of powder measurement which allows patient to dose according to medical indication the granulate for oral suspension according to the dosage stated in every case (2.5 to 5.0 grams).

The multiple dose granulates showed an appropriate taste upon reconstitution in water and stability in time.

EXAMPLE 6

The proceeding stated in EXAMPLE 1 was used, replacing the sodium bicarbonate (1680 mg) of the composition for an uniform mixture consisting of sodium bicarbonate (800 mg), potassium bicarbonate (700 mg) and anhydrous sodium carbonate (150 mg).

600 units of granulate for oral use were prepared, and packaged in single dose units.

One or more embodiments of the present invention have been described. Nevertheless, it will be understood that various modifications may be made without departing from the spirit and scope of the invention. Accordingly, other embodiments are within the scope of the following claims.

What is claimed:

1. Anti-acid pharmaceutical composition for the rapid and prolonged neutralization of gastric acidity with mucosa-protecting activity in powder form to prepared by dispersion in water, a pharmaceutical solution or suspension for oral use CHARACTERIZED in that the composition comprises:
   sodium alginate;
   an anti-acid soluble agent or a combination of anti-acids;
   a proton pump inhibitor;
   diluent and sweetening agents,
   wherein:
   a) 20 to 30% of sodium alginate present in the formulation along with the total of the proton pump inhibitor are homogeneously distributed over the surface of the total soluble anti-acid agent or of the combination of anti-acids of the composition; and
   b) the rest of sodium alginate present in the formulation contains a percentage of humidity of between 0.5 and 1.5%.

2. The composition according to claim 1, wherein the dispersion time in water is less than 2 minutes.

3. The composition according to claim 1, wherein the sodium alginate has a humidity content of less than 2%, after drying.

4. The composition according to claim 1, wherein the proton pump inhibitor is homogeneously distributed with part of the sodium alginate over the surface of the soluble anti-acid agent or a combination of anti-acids and remains stable at gastric pH for at least 30 minutes.

5. The composition according to claim 1, wherein the sodium alginate content is between 100 and 500 mg per dosage unit.

6. The composition according to claim 1, wherein the soluble anti-acids or combination of anti-acids are present in an amount between 100 and 2000 mg per dosage unit.

7. The composition according to claim 1, wherein each dosage unit contains from 10 to 80 mg of proton pump inhibitor.

8. The composition according to claim 4, wherein the proton pump inhibitor is selected from the group consisting of omeprazole, esomeprazole, pantoprazole, lanzoprazole and the corresponding salts thereof.

9. The composition according to claim 1, wherein the anti-acid agent is selected from the group consisting of potassium bicarbonate, sodium bicarbonate, sodium bicarbonate, calcium carbonate, magnesium carbonate, calcium hydroxide, aluminum hydroxide, and mixtures thereof.

10. The composition according to claim 5, wherein each dosage unit contains 250 mg of sodium alginate, 1680 mg of sodium bicarbonate as anti-acid agent and 20 mg of omeprazole.

11. The composition according to claim 5, wherein each dosage unit contains 250 mg of sodium alginate, 1680 mg of sodium bicarbonate as anti-acid agent and 30 mg of omeprazole.

12. The composition according to claim 5, wherein each dosage unit contains 250 mg of sodium alginate, 1680 mg of sodium bicarbonate as anti-acid agent and 40 mg of omeprazole.

13. The composition according to claim 5, wherein each dosage unit contains 250 mg of sodium alginate, 1680 mg of sodium bicarbonate as anti-acid agent and 15 mg of lansoprazole.

14. The composition according to claim 5, wherein each dosage unit contains 250 mg of sodium alginate, 1680 mg of sodium bicarbonate as anti-acid agent and 30 mg of lansoprazole.

15. The composition according to claim 5, wherein each dosage unit contains 250 mg of sodium alginate, 1680 mg of sodium bicarbonate as anti-acid agent and 20 mg of esomeprazole.

16. The composition according to claim 5, wherein each dosage unit contains 250 mg of sodium alginate, 1680 mg of sodium bicarbonate as anti-acid agent and 40 mg of esomeprazole.

17. The composition according to claim 5, wherein each dosage unit contains 250 mg of sodium alginate, 1680 mg of sodium bicarbonate as anti-acid agent and 20 mg of pantoprazole.

18. The composition according to claim 5, wherein each dosage unit contains 250 mg of sodium alginate, 1680 mg of sodium bicarbonate as anti-acid agent and 40 mg of pantoprazole.

19. Pharmaceutical preparation in powder form, either single dose or multiple dose, according to claim 1, wherein each dosage unit consists of 3 to 10 grams of the composition.

20. A pharmaceutical preparation according to claim 19, wherein a 5g dosage unit of granulate for oral suspension contains 5 to 10% of sodium alginate, 33.6% of sodium bicarbonate and 0.4 to 0.8% of proton pump inhibitor.

21. A composition according to claim 1, wherein the residual humidity of the pharmaceutical composition is less than 0.7%.

22. A composition according to claim 5, wherein the sodium alginate content is 250 mg per dosage unit.

23. Pharmaceutical preparation in powder form, either single dose or multiple dose, according to claim 19, wherein each dosage unit consists of 5 grams of the composition.

* * * * *